(12) United States Patent
Rappaport

(10) Patent No.: US 12,268,892 B2
(45) Date of Patent: Apr. 8, 2025

(54) ATTACHABLE LIGHT AND VIBRATION THERAPY SYSTEM FOR TREATMENT OF SKIN

(71) Applicant: MARCI BEAUTY INC, Las Vegas, NV (US)

(72) Inventor: Shaul Rappaport, Las Vegas, NV (US)

(*) Notice: Subject to any disclaimer, the term of this patent is extended or adjusted under 35 U.S.C. 154(b) by 1050 days.

(21) Appl. No.: 17/063,639

(22) Filed: Oct. 5, 2020

(65) Prior Publication Data

US 2022/0105359 A1   Apr. 7, 2022

(51) Int. Cl.
| | |
|---|---|
| A61N 5/06 | (2006.01) |
| A61F 13/00 | (2024.01) |
| A61F 13/12 | (2006.01) |
| A61H 23/00 | (2006.01) |

(52) U.S. Cl.
CPC .......... *A61N 5/0616* (2013.01); *A61F 13/124* (2013.01); *A61H 23/00* (2013.01); *A61F 2013/00659* (2013.01); *A61F 2013/00919* (2013.01); *A61H 2201/10* (2013.01); *A61H 2205/024* (2013.01); *A61N 2005/0652* (2013.01); *A61N 2005/0663* (2013.01)

(58) Field of Classification Search
CPC ................ A61H 23/00; A61H 2210/10; A61H 2210/1604; A61H 2210/165; A61H 2205/024; A61N 2005/0652; A61N 2005/0663; A61N 2005/0662

See application file for complete search history.

(56) References Cited

U.S. PATENT DOCUMENTS

| | | | |
|---|---|---|---|
| 9,744,378 B2 | 8/2017 | Tapper et al. | |
| 2012/0283623 A1* | 11/2012 | Tsao | A61N 5/0616 604/20 |
| 2014/0379050 A1* | 12/2014 | Pai | A61N 5/0619 607/88 |
| 2015/0182415 A1* | 7/2015 | Olkowski | A61H 23/02 604/295 |
| 2015/0290470 A1* | 10/2015 | Tapper | A61N 5/0616 607/91 |
| 2017/0238872 A1* | 8/2017 | Donnay | A61B 5/061 |
| 2017/0291007 A1* | 10/2017 | Dubey | A61H 23/02 |
| 2018/0099143 A1* | 4/2018 | Kim | A61N 1/0492 |
| 2019/0140110 A1* | 5/2019 | Zhao | H01L 21/02433 |
| 2021/0186803 A1* | 6/2021 | DiMino | A61N 5/0622 |
| 2022/0211162 A1* | 7/2022 | Kim | A45D 44/002 |

* cited by examiner

*Primary Examiner* — Colin W Stuart
*Assistant Examiner* — Douglas Y Sul
(74) *Attorney, Agent, or Firm* — Amburn Law PLLC; Dean W. Amburn

(57) ABSTRACT

A removably attachable phototherapy and vibration system for attachment to and treatment of skin beneath the eyes includes a therapeutic lamp platform for radiant lamps such as LEDs disposed in an assembly, and including a vibrating element, facing towards a patient and a plurality of light apertures substantially aligned with the LEDs for communicating lamp radiation from the lamps to a user. The lamps, vibrating element and associated circuitry are disposed so that the attachable surface is relatively smooth and seamless towards the patient. The system includes two devices one for the right and the other for the left eye of the user. Each device is attachable to beneath each eye with a suitable adhesive such as a reusable silicone strip. The system includes a charging dock for storing and charging the devices.

20 Claims, 7 Drawing Sheets

ATTACHABLE LIGHT AND VIBRATION THERAPY SYSTEM FOR TREATMENT OF SKIN

FIELD OF THE INVENTION

The invention generally relates to a device for delivering light and vibration-based treatments to areas of skin in proximity to a person's eyes. More particularly, the invention relates to a light and vibration therapy system including a device that is removably attachable to an area of skin underneath each eye.

BACKGROUND

As supported by studies, certain light spectrums emitted by LEDs (blue or red) are known to be therapeutic for skin including significantly improved skin complexion, skin feeling, skin roughness, and measured collagen density. See e.g. Daniel Barolet, "Regulation of Skin Collagen Metabolism in Vitro Using a Pulsed 660 nm LED Light Source: Clinical Correlation with a Single-Blinded Study" J Invest Dermatol, 2009 December. Treating skin around a person's eye is particularly advantageous to help decrease wrinkles and dark rings underneath the eye. However, treating an area around the eye with light poses special difficulties due to risk of light entering the eye and potentially causing injury. Further, the contours of each individual's face have a tendency to differ from one another.

Existing light treatment devices include a full or partial face mask generally offering a one-size-fits-all to the face of each user. For example, U.S. Pat. No. 9,744,378 discloses a mask device having a plurality of LED lights for treating a person's face with light. The mask includes a support frame appearing to be similar to a pair of glasses and including protective lenses presumably adapted to protect the wearer's eyes from injury by the light. Therefore, there remains a need to provide users/patients with a convenient at-home light therapy delivery device that does not require a wearable mask, veil or hood. Further, a need exists for a device that avoids the potential of damage to the eyes due to stray light emitted from LEDs in a mask held close to a person's face during treatments.

In addition, prior known light therapy devices, particularly masks, have suffered from problems relating to the exposure of the LEDs to contact with the user's skin. More particularly, in an effort to maximize light communication to a patient, the LEDs have been disposed in a manner which allow them to be physically engaged (e.g., touched) by a patient, or even contact a treatment surface, which presents the possibility of damaging the LEDs as a result of the accumulation of dirt and oil. In addition, any such contact with exposed LEDs and related wiring can be dangerous to patients who are exposed to the sharp or hot edges of the LEDs. In a mask embodiment, the exposure to LEDs and related circuitry presents an intimidating and unpleasant experience when the therapy requires several minutes of time for completion. The awkwardness is heightened when the mask is disposed relatively close to the face, often causing an uncomfortable, claustrophobic sensation over time to the patient.

A hands-free therapeutic experience is always better than having to hold the device in a particular position for extended periods of time during the therapy. Numerous assemblies have been conceived for mounting masks and helmet-like devices using a variety of straps, bands, wraps and cords, which can result in a pressing of the mask and support assembly closely against the face, hair or scalp of a patient. There is always a need to minimize the extent of such attachment assemblies so that on the one hand the subject device is securely attached on the patient, but also that the attaching structure has minimal consequence to the patient's comfort during the therapy itself. Being relatively light in weight, and easily supported during therapeutic use are important to consumer acceptance.

As users come in a variety of shapes and sizes, devices should be sized or adjustable so that the therapy can be efficiently applied and/or selectively intensified to desired treatment areas. Lastly, particularly in therapeutic devices treating facial areas, eye protection is needed to avoid light damage or irritation to a patient's eyes. Prior known devices have typically used separable patches which must rest on the eye area to block the therapeutic light from communication to the eye itself. There is a need for a better way that is readily adaptable to communicate therapeutic light to areas near the eyes, particularly with regard to anti-aging treatments, and still protect the patient.

It is desired to provide alternative means of using the benefits of the light therapy in a manner to maximize therapeutic efficiencies in exposure while maintaining ease and convenience of use. For this reason, a variety of light weight, flexible and adjustable embodiments are disclosed within this disclosure incorporating a variety of varying applications responsive to the user's conditions or needs. Finally, including a vibration feature allows for offering an invigorating treatment of the skin around a person's eyes. Existing vibration treatment devices have many of the same limitations as experienced with light treatment devices.

SUMMARY OF THE INVENTION

The present embodiments comprise light and vibration therapy systems and assemblies comprising a therapeutic light platform for radiant lamps such as LEDs disposed in a first and second attachable device with the first and second attachable device having a connecting surface adapted to adhere to a user's skin underneath each eye of the user. The first attachable device is separate from and not wired or mechanically connected to the second attachable device wherein each are separately attached to the user's skin. In an embodiment the first attachable device is a mirror image of the second attachable device.

The connecting surface is horizontally and vertically curved to approximate the curvature of the skin surface underneath the eyes. The first and second attachable device have a curved top and bottom edges that curve in approximate conformity with the lower portion of a person's eye orbitals. The first and second attachable device are small relative to the size of an average adult user's face. In an embodiment, the first and second attachment device are each less than 3 cm from the top edge to the bottom edge; less than 8 cm from right end to left end; 0.5 cm in thickness at any location along the curved body; and have a thickness from a top plane to a bottom plane of 1.5 cm. In an embodiment, the first and second attachable device when attached to a user's face underneath each eye approximate the appearance of wings underneath the eyes.

The first and second attachable device are operated wirelessly thus allowing for adherence to a user's eye area without the limitation of a wired connection to a power or control source. The connecting surface has openings for the lamps such as LEDs. The connecting surface is separated from the user's skin by an adhesive. In an embodiment the adhesive is a layer of adhesive material that covers the connecting surface and creates a barrier between the connecting surface and the skin of the user. The layer of adhesive material is translucent or transparent thus allowing light from the radiant lamps to travel through the adhesive material and treat the user's skin.

In an embodiment the assembly includes a vibration mechanism adapted to vibrate in different modes of vibration thus offering an additional treatment of the tissue underneath the eye of the user.

In another embodiment a controller is disposed in the first and second attachment body and is adapted to control the radiant lamps and the vibration mechanism. The controller can be adapted to pulse the radiant lamps or adjust the intensity and timing of a light emitting from the radiant lamps. The controller can be adapted to control and pulse a vibration of the vibration mechanism. The first and second attachable devices include a battery disposed therein. The battery is rechargeable and connectable to a battery charger. The first and second attachable devices also include a button or switch for activating the light and vibration features. In a further embodiment, a remote controller such as a handheld remote controller is adapted to control the device including control of the light and vibration features of the device.

In an embodiment the system further includes a storage case for holding and recharging the battery of the first and second attachable devices. The storage case includes receptor area adapted to receive and hold the first and second attachable devices. The receptor area includes a charging connector and interfaces with a charging connector on the first and second attachable devices thus allowing for recharging the battery in the first and second attachable devices while in storage. The storage case includes an inlet for accepting a charging cord that is pluggable into a power source.

The present embodiments comprise an adjustable/flexible platform for providing a light-based therapy that is adaptable to the user's receptive skin surfaces beneath the eyes, and adaptable to fit different sized users, wherein the light therapy can be applied without limitation of the kind of light and without limitation of the ultimate purpose of the therapy, i.e., beauty, health, and/or wound healing. Such sources can vary in the form of the radiant energy delivery. Pulsed light (IPL), focused light and other methods of manipulating light energy are encompassed within the present embodiments. Other methods of light emission may comprise continuous, pulsed, focused, diffuse, multi-wavelength, single wavelength, visible and/or non-visible light wavelengths.

A present embodiment describes forms such as wing shaped devices adapted to attach to the skin underneath each of the user's eyes with LED light emitted from LED bulbs or LED strips that are capable of being adjusted to accommodate the variances in areas intended for therapeutic attention. Control systems are included to vary light intensity, frequency or direction.

The platform is secured underneath the user's eyes with an adhesive such as an adhesive material or strip of adhesive such as a silicone strip. The adhesive strip is applied to the connecting surface which in turn is connected to the user's skin area underneath each eye. The adhesive strip is cleanable at the site of connection to the skin of the user and thus reusable for multiple applications with adequate adherence to the user's skin. Thus, through application of the adhesive strip the light therapy can be maximized while keeping clean the contact surface including the lights disposed therein.

The inclusion of a controller allows for adjustability implemented through "smart" processing and sensor systems for enhanced flexibility/adjustability in the form of adjustable energy output, adjustable wavelengths, timers, and the like. In an embodiment, the system will have the ability to evaluate the skin of the patient with sensors for color, wrinkles, and the like, and plan a smart treatment, utilizing more or less energy on the priority zones. The subject embodiments can be smart from the standpoint of skin type, age, overall severity of problems and have the ability to customize the treatment accordingly.

The present disclosure thus describes a compact, light weight, fully flexible and adjustable LED system and assembly which provides improved usability and light dispersion for treatment of skin areas under a user's eyes.

BRIEF DESCRIPTION OF THE DRAWINGS

Advantages of the invention will be readily appreciated as the same becomes better understood by reference to the following detailed description when considered in connection with the accompanying drawings, wherein.

DETAILED DESCRIPTION OF THE DRAWINGS

The subject embodiments of the invention relate to a phototherapy and vibration system including methods and devices comprising a wearable hands-free device for attaching to the skin of the user underneath the user's eyes. The subject system and devices provide numerous benefits including a light platform wherein the platform and the lamps therein are positionable relative to the user's eyes with no requirement to be held in place by the user or other means apart from an adhesive layer between the devices and an area of skin under the user's eyes. The devices are compact and light weight thus offering the user a comfortable platform for receiving light and vibration therapy treatments. The occurrence of light from the light platform inadvertently entering the user's eyes is minimized, if not prohibited by the light platform interfacing with the user's skin rather than sitting a distance away from the skin. The structural assembly of the devices precludes sharp or hot surfaces from being engageable by the user as the lamps are recessed in a surface that contacts with the user's skin and are separated from the skin by the adhesive layer. The lamps and associated wiring, battery and controller are enclosed in a discreet and aesthetically pleasing body. The overall assembly is purposefully constructed for ease of user use and comfort.

Figure 1:
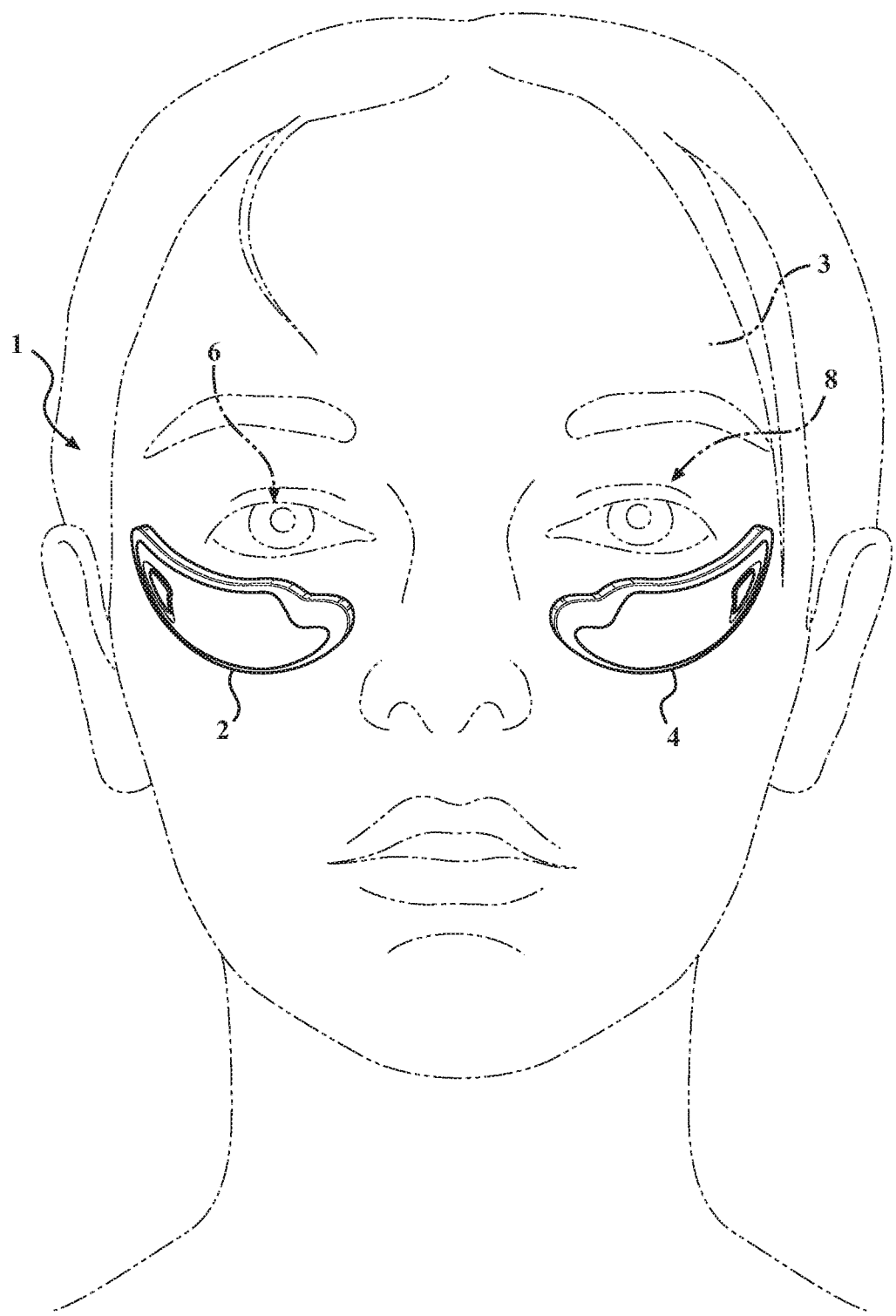
FIG. 1 is a perspective view of the first and second attachable devices of an embodiment of the invention in the environment of attachment to an exemplary user's face.

More particularly, with reference to FIG. 1 the subject embodiments of the phototherapy and vibration system 1 of the invention comprise a first attachable device 2 and a second attachable device 4 for attachment under the eyes of a user 3. All references to the user 3 (sometimes referred to as a patient) or the user's eyes are for environmental purposes of describing how the invention is used and, not as a claimed element, or otherwise a part of the invention disclosed herein.

The first attachable device 2 and second attachable device 4 are separate devices capable of working separately or together. For example, the user may elect to treat only one eye with the first attachable device 2. The first attachable device 2 is shaped to contour to the underside of the user's right eye 6 and the second attachable device 4 is shaped to contour to the underside of the user's left eye 8. As a result of being separate devices that attach to a user's face, the system 1 offers advantages including an ability to adapt to a wide variance in shape, structure and size of the user's face. Further, there is no requirement to include adjustment capabilities such as straps, a frame, or other means of adjusting a treatment device to fit a particular user's face.

With added reference to FIGS. 2-7 the first and second attachable devices 2, 4 are described with reference to both devices having the same shape, size and assembly components. The first attachable device 2 is effectively a mirror image of the second attachable device 4. For benefit of simplifying the description of embodiments of the invention the first and second attachable devices 2, 4 are described with the same reference numbers to identify shared components and features. However, it should be appreciated that in embodiments, one of the devices could be a different shape, size or have different assembly components or features from the other.

Figure 2:
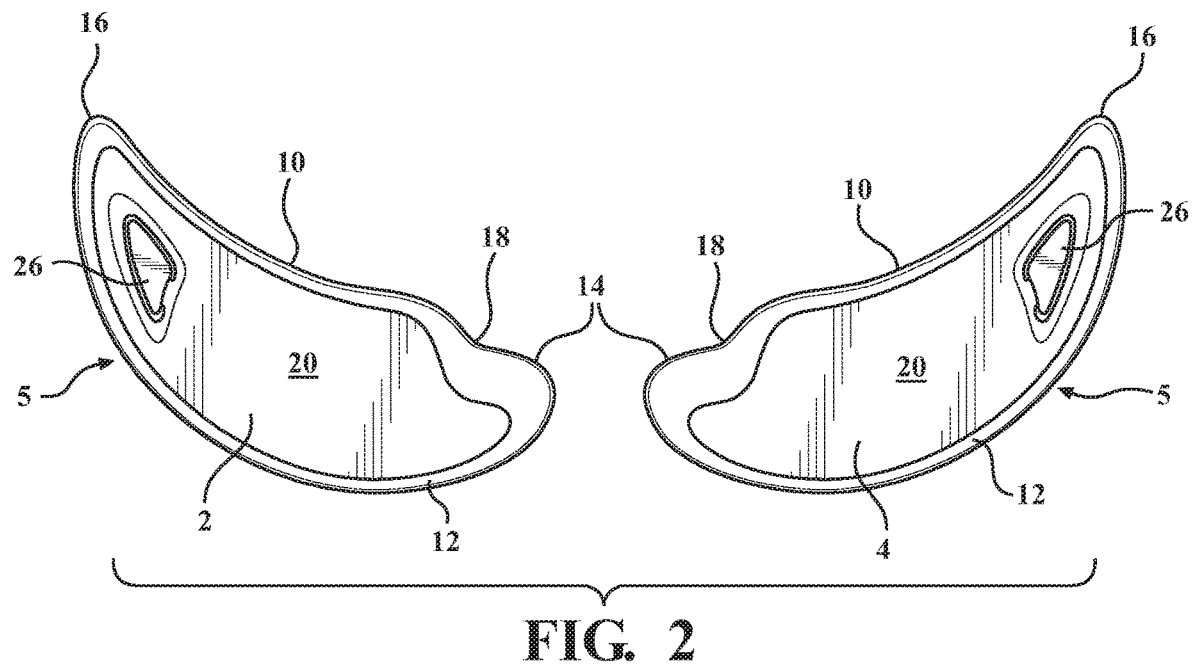
FIG. 2 is front view of the devices of FIG. 1.
Figure 3:
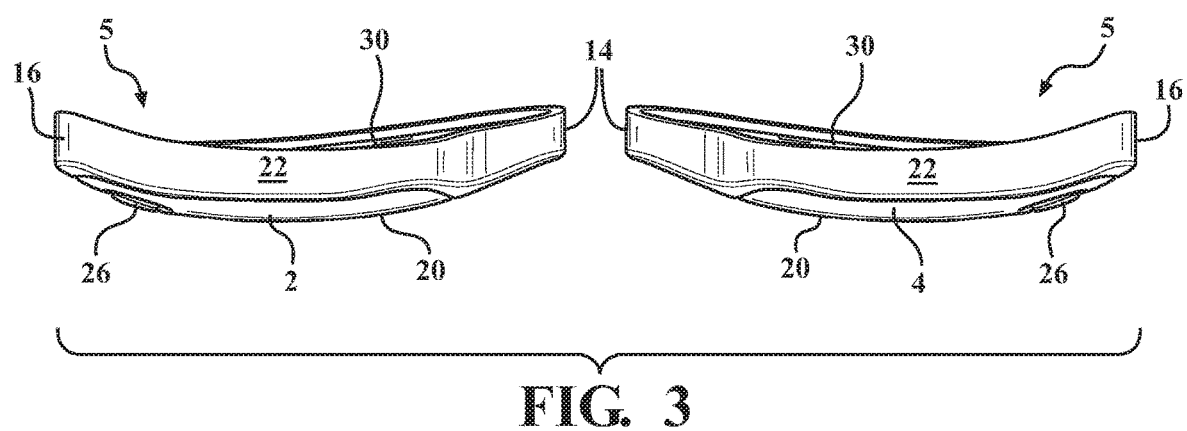
FIG. 3 is top view of the devices of FIG. 2.
Figure 4:
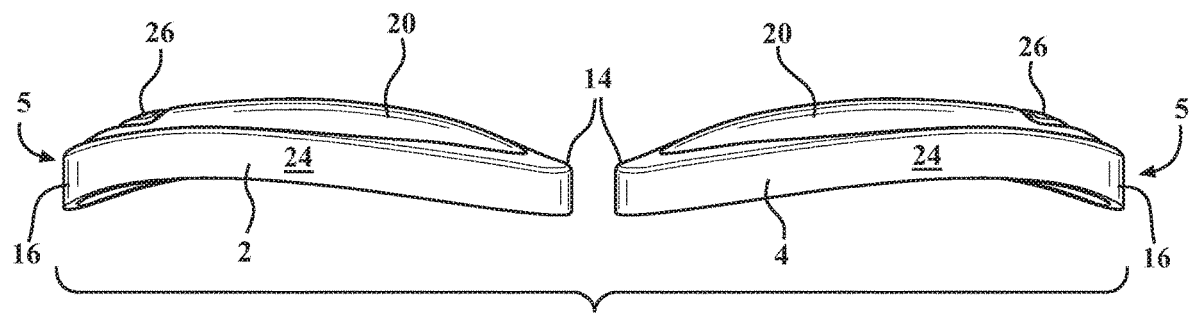
FIG. 4 is a bottom view of the devices of FIG. 2.
Figure 5:
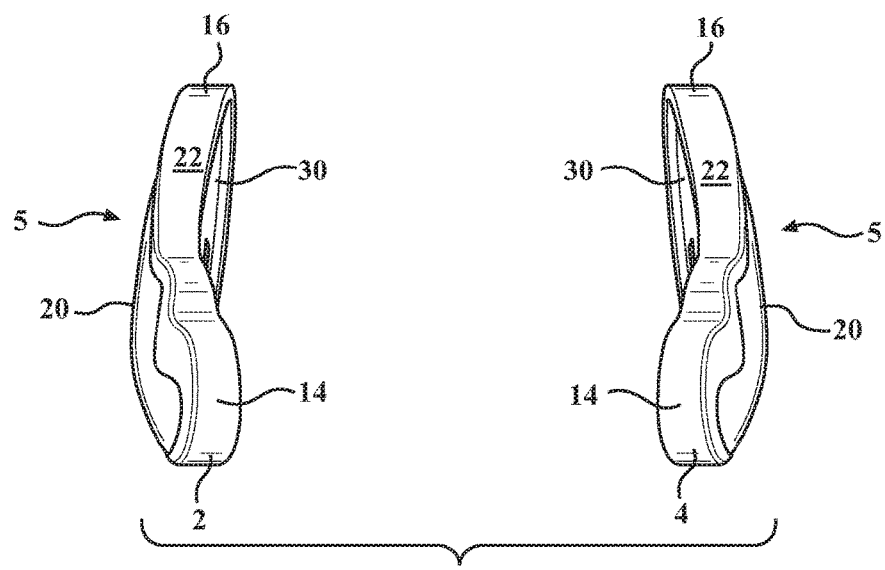
FIG. 5 is an angular side view of the devices of FIG. 2.
Figure 6:
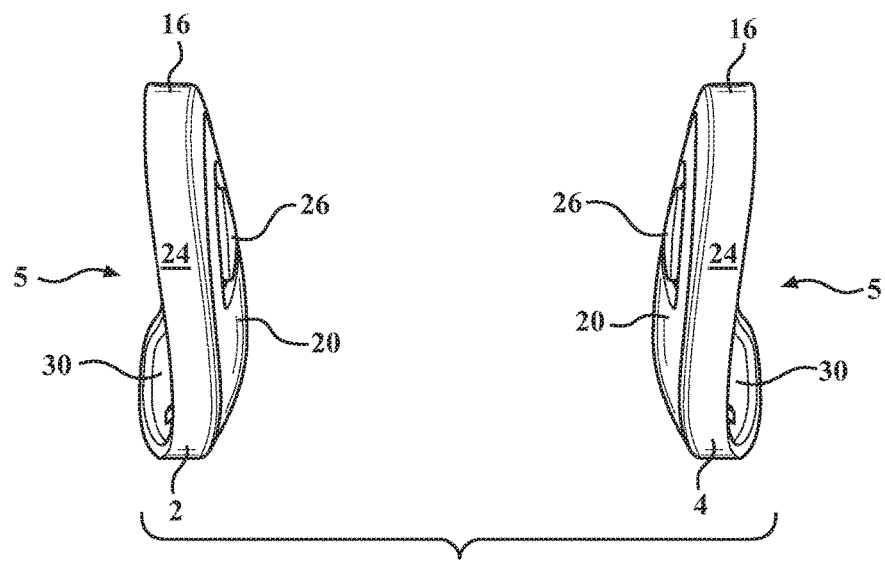
FIG. 6 is an angular opposite-side view of the devices of FIG. 2.
Figure 7:
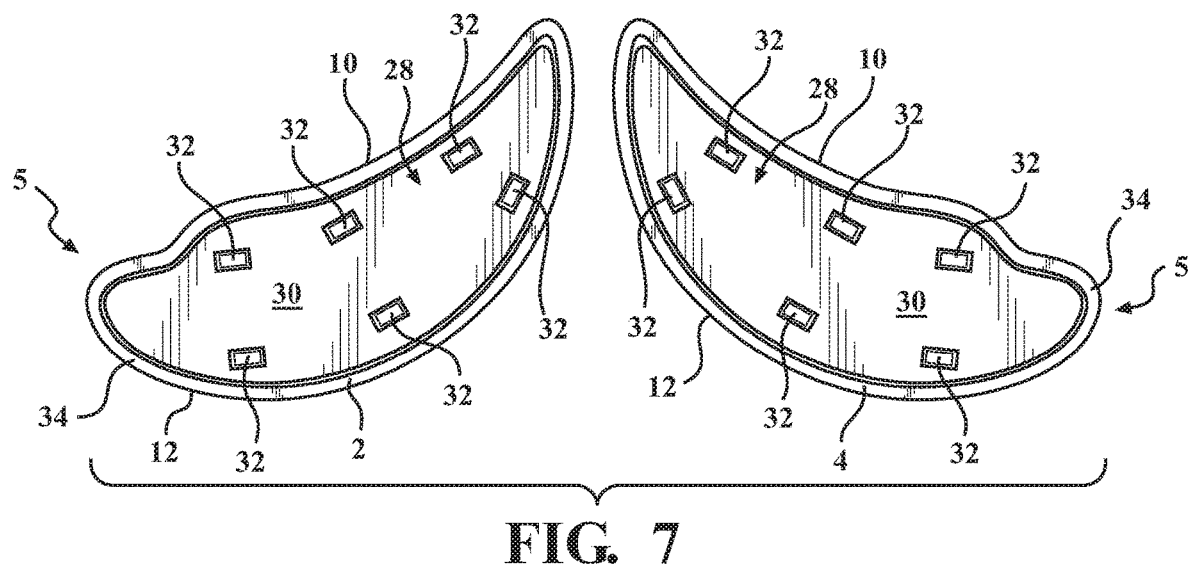
FIG. 7 is a back-side view of the devices of FIG. 2.

The first and second attachable devices 2, 4 include a frame 5 that is injection molded into one or more parts out of acrylonitrile butadiene styrene (ABS). The use of ABS allows the devices 2, 4 to be thin, light weight, and strong. The devices 2, 4 are shaped like wings (as seen in FIGS. 1 and 2). This wing-shape formation includes a concave top edge 10 between an inner end 14 and an outer end 16 and a convex bottom edge 12 between the inner end 14 and the outer end 16. The top edge 10 and the bottom edge 12 meet to form the inner end 14 and the outer end 16. A recessed portion 18 proximate to the inner end 14 further accentuates the wing-shape of the first and second attachable devices 2, 4. The wing-shape formation offers aesthetic benefits apart from functional advantages which include allowing for a discrete device that conforms to the underside of a user's eyes in an area that is known to have dark circles and inflammation, otherwise identified as periorbital dark circles.

The devices 2, 4 include a front surface 20, top portion 22 and bottom portion 24. Disposed in the front surface 20 is a button 26 for turning on/off the device and controlling the function of the device as explained in greater detail in reference to FIG. 9 below. In an embodiment, the button 26 can be located on a different portion of the device, or is missing entirely in favor of a remote-control system commonly known to those skilled in the art. In an embodiment, the devices 2, 4 are each less than 3 cm from the top edge 10 to the bottom edge 12; less than 8 cm from the inner end 14 to the outer end 16; 0.5 cm in thickness at any location along the curved body; and have a thickness from a top plane to a bottom plane of 1.5 cm.

The first and second attachable devices 2, 4 further include a light platform 28 disposed on a back surface 30 (treatment side) of the devices. The back surface 30 is concave inwardly towards the front surface 20 between the inner end 14 and the outer end 16 (as seen in FIGS. 3-6). More particularly, the treatment side of the devices are formed to conform to an average person's face underneath the eyes. As will be discussed, this concave, if not parabolic shape, allows the devices to better adhere to the skin of the user underneath the user's eyes.

The light platform 28 comprises a plurality of therapeutic lamps 32, such as red and blue LEDs. Other radiant energy forms could also include fluorescents, lasers or infrareds. Such sources can vary in the form of the radiant energy delivery. Pulsed light (IPL), focused light (lasers) and methods of manipulating light energy are encompassed within the present embodiments. Other methods of light emission may comprise continuous, pulsed, focused, diffuse, multi-wavelength, single wavelength, visible and/or non-visible light wavelengths.

Rather than placing the plurality of lamps 32 randomly, the subject LEDs are specifically minimized in number and disposed relative to the treatment areas under a user's eyes. It can be seen that the individual lamps 32 are disposed to treat the most common areas benefiting from the therapy. The LEDs would typically comprise blue LEDs in combination with red LEDs but could include one type of LED over the other. A combination of LED types allows for offering different treatment benefits. For example, LEDs in a red frequency are most useful for acne treatment.

Figure 8:
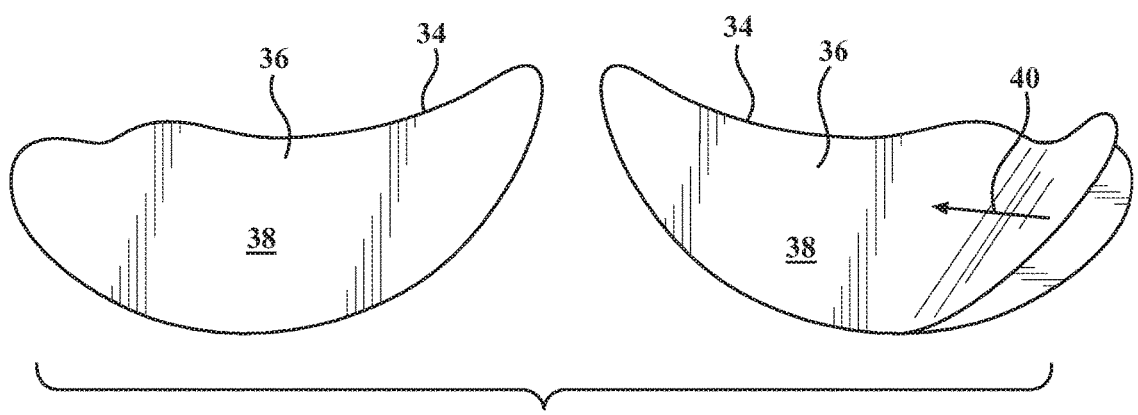
FIG. 8 is a perspective view of adhesive strips of the system of the invention.

Now adding reference to FIG. 8, the system 1 includes an adhesive 34 for attaching the first and second attachable devices 2, 4 to the skin of the user underneath and in proximity to the user's eyes. The adhesive 34 is preferably transparent or at least translucent to allow light from the light platform 28 to reach the user's skin. Preferably the adhesive 34 is suitable for contacting the skin of the user with minimized detrimental consequence to the user's skin, and includes those adhesives in this category known to those skilled in the art. In a preferred, but nonlimiting embodiment, the adhesive 34 includes silicone or a silicone composition. The silicone is a medical grade hypo-allergenic silicone. The silicon will advantageously hold the devices 2, 4 tightly on the skin of the user even when the user is moving, jumping or with the devices vibrating. Again, other types of adhesives known to those skilled in the art are suitable for use with the system 1.

In a preferred, but nonlimiting embodiment, the adhesive 34 is preformed into strips of material 36 and includes a cover 38 on the front and backside (not seen) of the adhesive 34 strips. The cover 38, typically made out of a plastic or plastic coated paper, is easily peeled away 40 thus leaving the adhesive strip 34 ready for application onto the back surface 30 of the first and second attachable devices 2, 4. As seen in FIG. 8 the adhesive strip 36 is advantageously in the same shape and approximate size as the back surface 30 of the first and second attachable devices 2, 4. This feature provides an easy and convenient way to apply the adhesive 34 before attaching the first and second attachable devices 2, 4 to the skin of the user.

It should be appreciated that the adhesive 34 creates a sealed connection with the skin of the user thus preventing stray light from leaving the devices 2, 4 and entering the user's eyes. Further, by pressing the devices 2, 4 onto the skin underneath each eye the adhesive 34 attaches to the skin and conforms the skin to the back surface 30 of the devices. Advantageously, this form of attachment allows the back surface 30 of the treatment devices 2, 4 to not need to exactly match the contours of each user's face around the user's eyes.

In the example of using a strip of silicone as the adhesive 34, the silicone strip offers the advantage of being reusable for several applications to the skin during multiple discrete treatments with the system. Further, once the silicone strip is attached to the back surface 34, the opposing surface that contacts the skin of the user can be cleaned between treatments without losing its useful stickiness. This ability offers distinct advantages of reducing cost and waste that otherwise would apply to using a new layer of adhesive for each treatment.

In a nonlimiting embodiment, the first and second attachable devices 2, 4 include a flange or lip 34 extending around the parameter of the light platform 28. The flange or lip 34 creates a spacing between the skin of the user and the light platform 28 particularly in the areas around the parameter of the light platform 28. In this embodiment, the adhesive strip of material 36 fits on the back surface 30 within the boundaries of the flange or lip 34 and creates a substantially flush surface between the user's skin and the adhesive layer connecting to the user's skin.

Figure 9:
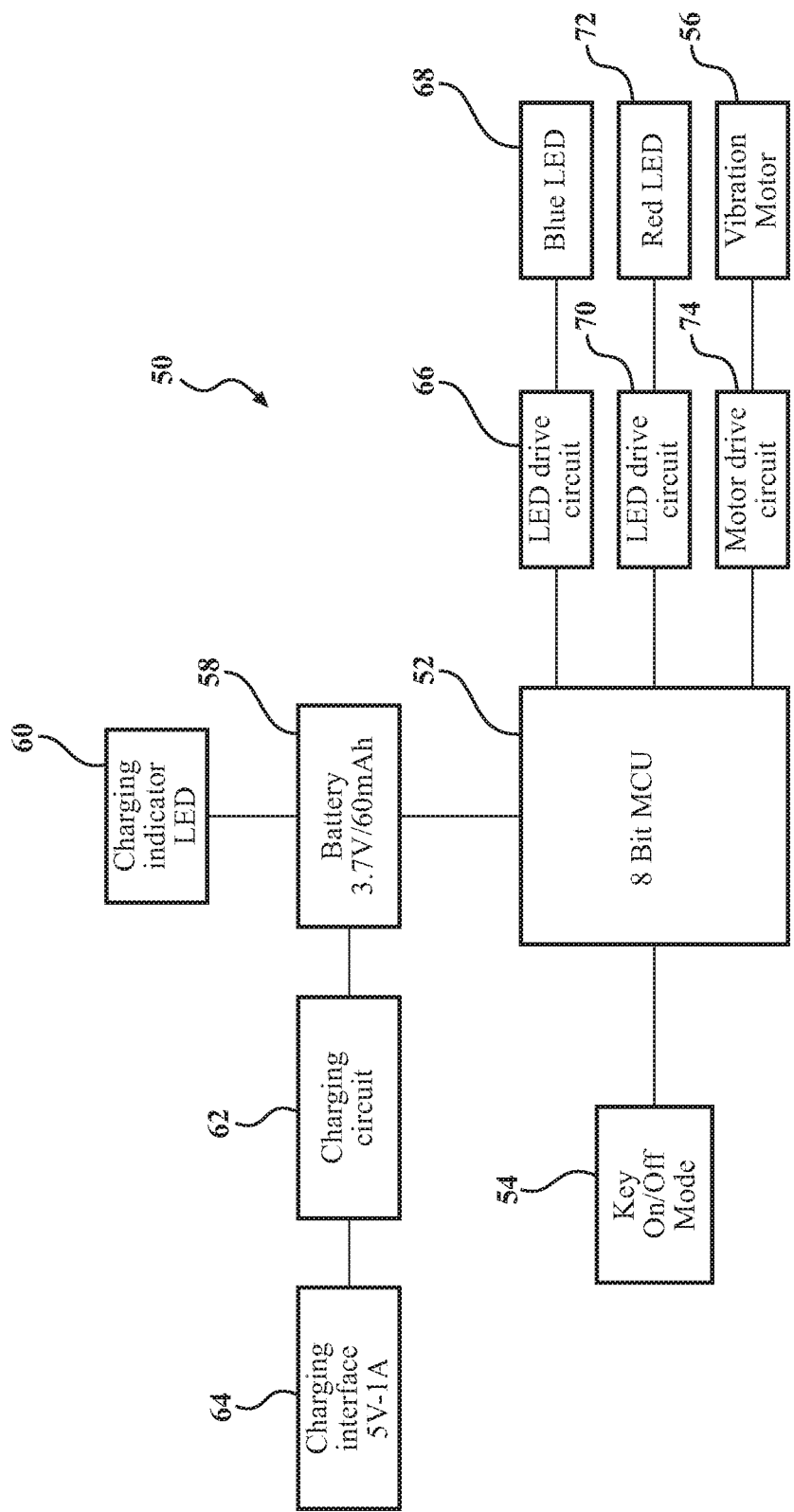
FIG. 9 is a schematic of the devices of FIG. 2.

With additional reference to FIG. 9, the first and second attachable devices 2, 4 include electrical and mechanical components 50 that are substantially enclosed and disposed in the body of the devices between the front surface 20 and the back surface 30. The mechanical and electrical components 50 are well known to those skilled in the art including differing components or the arrangement of the components. While it is assumed that the components will be in communication with each other via wiring, other modes of communication are contemplated including the potential that more than one component is combined with another.

The electrical and mechanical components 50 include a microcontroller (MCU) 52. The microcontroller 52 includes or is in communication with a nonvolatile memory (not shown) and is programmed with a programming language to function for purposes of operating the devices as described herein. The microcontroller 52 is in communication with a mode switch 54. The mode switch 54 is controlled by the user actuating the button 26. The microcontroller 52 detects the mode switch 54 to switch the device's mode including on or off, and between modes such as modes of lighting emitting from the light platform 28 and vibration modes emitting from a vibration motor 56. For example, in a nonlimiting embodiment, pressing the button 26 for a period of time such as 3 seconds switches the device off while briefly pressing the button 26 for a shorter prior of time such as 1 second, or less causes the device to progress through different lighting and vibration modes. For example, the different modes include turning the lamps 32 on for continual lighting, or in an alternative mode having the lamps strobe. Other modes include continual vibration or pulsed vibration. Additional modes include activating the lamps 32 and vibration features to work simultaneously. The device enters standby mode after turning it off. More modes of operation of the devices 2, 4 are contemplated to be within the scope of the embodiments contained herein.

The microcontroller 52 is also in communication with a battery 58 suitable for powering the devices 2, 4. For example, the battery 58 could be a 3.7V lithium-ion battery with a capacity of 60 mAh. The battery 58 is equipped with a protection board, which has the functions of short circuit protection and low voltage protection. The battery 58 is in communication with a charging indicator LED 60 suitable for indicating whether the battery 58 is charged by showing a green light or a red light when needing to be charged. The battery 58 is also in communication with a charging circuit 62 which is in communication with a charging interface 64 such as a 5V-1 A interface known to those skilled in the art. The charging interface 64 is externally accessible in the devices 2, 4.

The microcontroller 52 is also in communication with a first LED drive circuit 66 which is in communication with a blue LED; a second LED drive circuit 70 which is in communication with a red LED 72; and a motor drive circuit 74 in communication with the vibration motor 56, adapted to vibrate the device when activated. The microcontroller 52 controls the blue LED 68, red LED 72, and vibration motor 56 through a general-purpose input/output (GPIO) port on the microcontroller 52.

As previously described, the system 1 is designed to work with variety of different lighting sources. This includes different LEDs. In a nonlimiting embodiment, the devices 2, 4 are preferred to work with LEDs offering a light wavelength between 475-645 nm which has anti-aging treatment benefits. In nonlimiting embodiments, the LED colors include red, blue/purple, amber and green together with combinations thereof.

Figure 10:
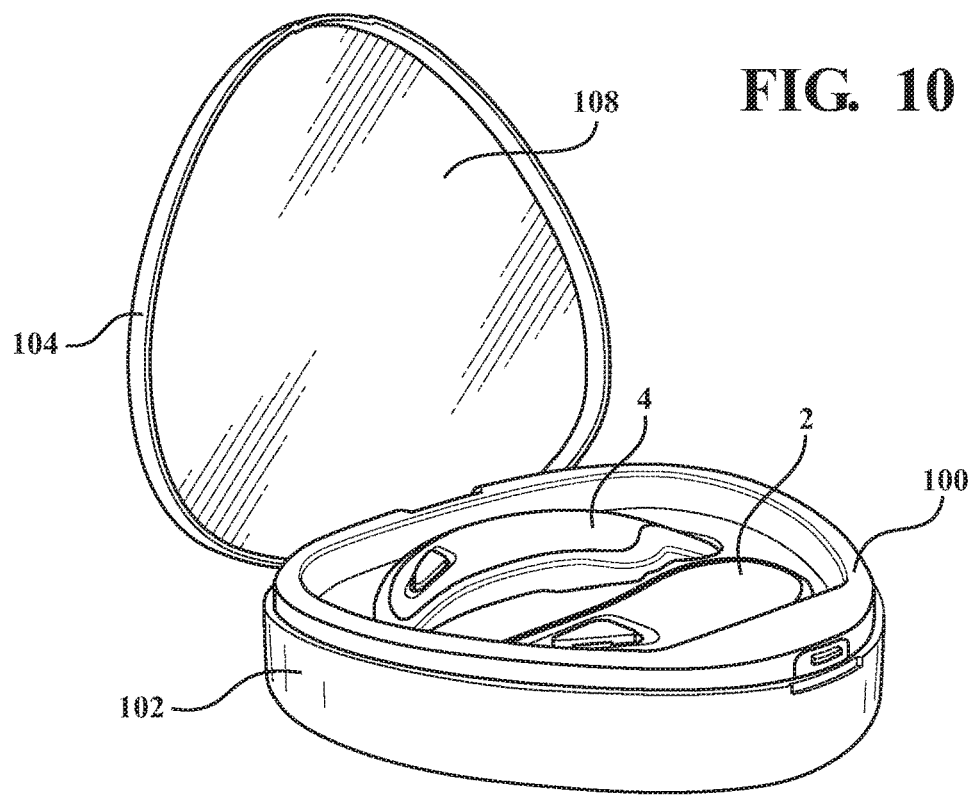
FIG. 10 is a perspective view of an embodiment of the system of the invention including the devices of FIG. 2, in a charging dock.
Figure 11:
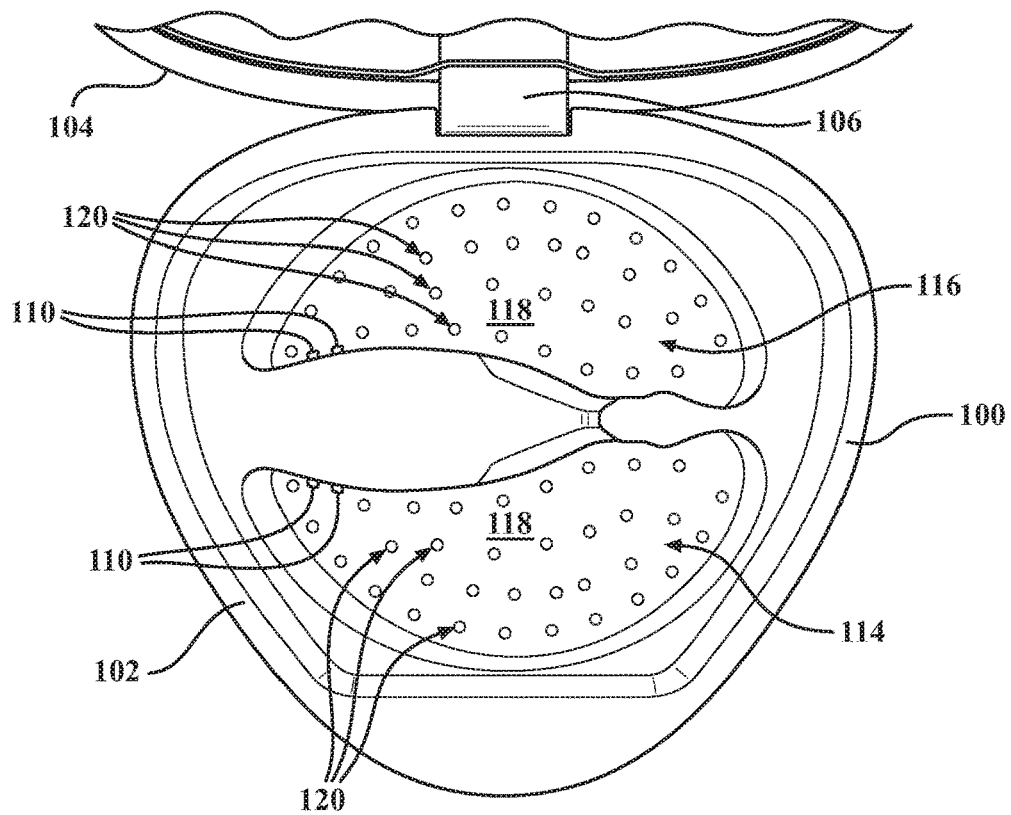
FIG. 11 is a top perspective view of the charging dock of FIG. 10 without the devices.
Figure 12:
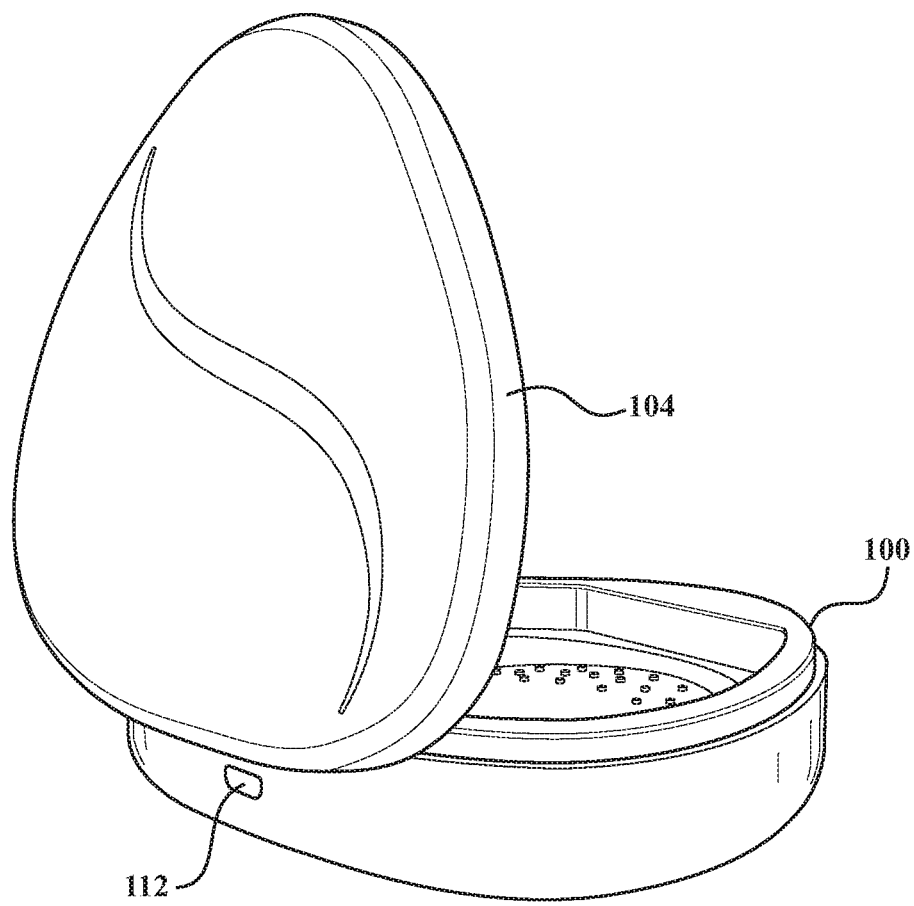
FIG. 12 is a back-side perspective view of the charging dock of FIG. 10.

With further reference to FIGS. 10-12, in a nonlimiting embodiment, the system 1 includes a charging dock 100 for receiving, storing and charging the battery 58 in the devices 2, 4. The charging dock includes a base 102 and a lid 104. A hinge 106 between the base 102 and the lid 104 allows the user to easily open and close the storage unit to protect and have easy access to the devices 2, 4. The charging dock 100 includes a mirror 108 in the lid 104 which advantageously allows the user to see how the devices 2, 4 are positioned on the user's face. The charging dock 100 is made from ABS and includes more than one ABS manufactured component assembled together.

The charging dock 100 includes charging connectors 110 adapted to contact with the charging interface 64 on the devices 2, 4. The charging connectors 110 are in wired (not shown) connection with a charging port 112 on a back side of the charging dock 100. The charging port 112 is of type known to those skilled in the art and alternatively includes a USB or micro-USB type connection.

The charging dock 100 includes a first charging bay 114 adapted to be of the same shape but slightly larger in size as the first attachable device 2, and a second charging bay 116 adapted to be of the same shape but slightly larger size as the second attachable device 4. The shape and form of the first and second charging bay 114, 116 facilitates the connection between the charging connectors 110 and the charging interface 64 in the first and second attachable devices 2, 4. The first and second charging bays 114, 116 include a support surface 118 which substantially matches the shape and curvature of the back surface 30 of the devices 2, 4 which, again, facilitates holding the devices securely, but not permanently in the charging bays. The support surface 118 includes a plurality of dimples 120 (or protrusions). The dimples 120 help maintain a spacing between the support surface 118 and the back surface 30 of the devices 2, 4. Alternatively and advantageously, once the user has applied a silicone strip to the back surface 30 of the devices 2, 4 and stores the devices in the charging dock 100, the dimples 120 create a separation between the silicone strip and the support surface 118 thus allowing for storage and easy removal of the devices without interfering with the silicone strip on the devices.

To use the system 1, the user would remove the first and second attachable devices 2, 4 from the charging dock 100 where they are stored and charged. The user would then apply an adhesive strip of silicone to the back surface 30 after removing a protective material on both sides of the silicone strips. Next, the user positions the devices onto the user's undereye area where the devices will attach and can begin a treatment process. The user can press the button 26 on each device to activate the devices to provide different modes of light and vibration treatment. When the treatment is completed the user will simply remove the devices from the user's face and return them to the charging dock 100. It is expected that the user can obtain upwards of 30 treatments using the same silicone strip and can clean the strips between treatments. Thus, the user will have a hand-free, convenient and beneficial treatment system to prevent and reduce aging signs like fine lines and wrinkles around the eyes. Optional vibration treatments help increase blood circulation and activates the orbicularis oculi muscles. The treatments help decrease the visibility of under eye inflammation (puffiness) and dark circles. The treatments offered by the system will help produce more collagen within the skin in the treatment area. Further, the system reduces if not eliminates the potential for light from the devices entering the lenses of the user's eyes.

The invention has been described in an illustrative manner. It is to be understood that the terminology, which has been used, is intended to be in the nature of words of description rather than of limitation.

Many modifications and variations of the invention are possible in light of the above teachings. Therefore, within the scope of the appended claims, the invention may be practiced other than as specifically described.

The invention claimed is:

1. A phototherapy treatment system adapted to attach to skin surfaces on the underside of a user's eyes, the system comprising:
    a first treatment device adapted to attach to a user's skin underneath the user's right eye and a second treatment device adapted to simultaneously attach to the user's skin underneath the user's left eye, wherein the first and second treatment device are not physically connected to each other, wherein the first and second treatment device comprise a concave top edge and convex bottom edge that meet at an inner point and outer point of the first and second treatment device, wherein proximate to the inner point is a recessed portion, wherein the recessed portion is adapted to conform to an inner portion of the user's eyes, wherein the first and second treatment device comprise a horizontally and vertically curved connecting surface, wherein the connecting surface includes a light platform having a plurality of LED lights disposed therein wherein the connecting surface of the first and second treatment device are removably attachable to the user's skin with an adhesive.

2. The system as set forth in claim 1, wherein the first and second treatment device further comprise a vibration motor disposed in the first and second treatment device, wherein the vibration motor is adapted to provide a vibration treatment to the user.

3. The system as set forth in claim 2, wherein the first and second treatment device further comprising a controller adapted to control the LED lights and vibration motor, wherein the controller provides different modes of treatments with the LED lights including a treatment mode combining a light and a vibration treatment.

4. The system as set forth in claim 1, further comprising an adhesive adapted to be applied to the connecting surface of the first and second treatment device.

5. The system as set forth in claim 4, wherein the adhesive is a silicone-based adhesive.

6. The system as set forth in claim 4, wherein the adhesive is in the form of an adhesive strip approximating the shape of the connecting surface of the first and second treatment device.

7. The system as set forth in claim 6, wherein the adhesive strip has a removable protective covering adapted to be removed prior to application of the adhesive strip onto the connecting surface of first and second treatment device.

8. The system as set forth in claim 1, wherein the first and second treatment device further comprise a controller adapted to control the LED lights, wherein the controller provides different modes of treatments with the LED lights.

9. The system as set forth in claim 1, further comprising a docking station adapted to hold the first and second treatment device and recharge a battery in the first and second treatment device wherein the docking station comprises a receiving section that substantially matches the shape of the first and second treatment device.

10. A phototherapy and vibration treatment system adapted to attach to the underside of a user's right and left eyes, the system comprising:
    a first and second treatment device having a horizontally and vertically curved connecting surface adapted to approximate a curvature of a skin surface underneath the user's right and left eyes including at least a portion of the user's right and left cheekbones, wherein the first and second treatment device comprise a concave top edge and convex bottom edge that meet at an inner point and outer point of the first and second treatment device, wherein proximate to the inner point is a recessed portion, wherein the recessed portion is adapted to conform to an inner portion of the user's eyes, wherein the first and second treatment device are adapted to adhesively attach to the skin surface underneath the user's right and left eyes, wherein the first and second treatment device are not physically associated with each other and are adapted to simultaneously attach to the skin surface underneath the user's right and left eyes;
    a plurality of LEDs disposed in the first and second treatment device;
    a vibration motor disposed in the first and second treatment device;
    a controller disposed in the first and second treatment device wherein the controller is adapted to control the LEDs and the vibration motor to provide different modes of light and vibration treatments; and
    an adhesive adapted to be applied to the connecting surface of the first and second treatment device wherein, the adhesive provides a releasable attachability between the first and second treatment device and the user.

11. The phototherapy and vibration treatment system of claim 10, wherein the adhesive includes at least one of silicone and a silicone composition.

12. The phototherapy and vibration treatment system of claim 10, wherein the adhesive is an adhesive strip having a removable covering.

13. The phototherapy and vibration treatment system of claim 10, wherein the adhesive is a silicone adhesive strip, wherein the side of the silicone adhesive strip that comes into contact with the user is cleanable and reusable for repeated treatments, including reattaching the first and second treatment device to the user.

14. The phototherapy and vibration treatment system of claim 10, further comprising a docking station adapted to store the first and second treatment device and charge a battery in the first and second treatment device.

15. The phototherapy and vibration treatment system of claim 10, wherein the plurality of LEDs comprise red and blue LEDs.

16. The phototherapy and vibration treatment system of claim 10, wherein at least some of the plurality of LEDs emit a light wavelength in the range of 475-645 nm.

17. The phototherapy and vibration treatment system of claim 10, wherein the first and second treatment device further comprise a switch adapted to turn on the first and second treatment device.

18. The phototherapy and vibration treatment system of claim 10, wherein the first and second treatment device are adapted to provide a plurality of light and vibration treatment modes of operation.

19. A phototherapy and vibration treatment system, comprising:
a first and second attachable treatment device adapted to releasably and adhesively attach to the underside of a user's right and left eyes, wherein the first and second treatment device comprise a body having a concave top edge, a convex bottom edge, and a horizontally and vertically curved treatment surface wherein the concave top edge and convex bottom edge meet at an inner point and outer point of the body, wherein proximate to the inner point is a recessed portion, wherein the recessed portion is adapted to conform to an inner portion of the user's eyes, wherein a plurality of LEDs are disposed in the body and adapted to emit light through a plurality of openings in the treatment surface, wherein a vibration motor is disposed in the body, wherein a controller is in operational communication with the LEDs and the vibration motor, wherein a battery is disposed in the body and in communication with the plurality of LEDs and the vibration motor.

20. The system of claim 19, further comprising a storage container wherein the storage container comprises a receiving section adapted to receive the first and second attachable treatment device, wherein the receiving section comprises a charging port adapted to contact a charging connector on the first and second attachable treatment device when the first and second treatment device are stored in the storage container, wherein the storage container is adapted to store and charge the battery of the first and second treatment device.

* * * * *